United States Patent [19]

Aisaka et al.

[11] Patent Number: 5,021,770

[45] Date of Patent: Jun. 4, 1991

[54] IMAGE DISPLAY SYSTEM AND DATA INPUT APPARATUS USED THEREIN

[75] Inventors: Kazuo Aisaka, Bunkyo, Japan; Akihide Hashizume, Taby, Sweden; Takakazu Huno, Nishitama, Japan; Ryuichi Suzuki, Kokubunji, Japan; Kazuko Terada, Suginami, Japan

[73] Assignee: Hitachi, Ltd., Tokyo, Japan

[21] Appl. No.: 217,931

[22] Filed: Jul. 12, 1988

[30] Foreign Application Priority Data

Jul. 15, 1987 [JP] Japan .................. 62-176735
Jul. 30, 1987 [JP] Japan .................. 62-191194

[51] Int. Cl.⁵ .................. G09G 3/02; G09G 1/02; H04N 5/32; H05G 1/64
[52] U.S. Cl. .................. 340/709; 340/799; 358/111; 378/99
[58] Field of Search .............. 340/707, 708, 709, 710, 340/750, 799, 721, 712; 358/111; 378/99, 98, 100, 901; 364/413.22; 250/337

[56] References Cited

U.S. PATENT DOCUMENTS 3,993,861 11/1976 Baer ...................... 340/707
4,245,244 1/1991 Lijewski et al. ........... 340/706
4,413,314 11/1983 Slater et al. .............. 340/712
4,700,299 10/1987 Kimura et al. ............. 378/99

Primary Examiner—Alvin E. Oberley
Assistant Examiner—Chanh Nguyen
Attorney, Agent, or Firm—Antonelli, Terry, Stout & Kraus

[57] ABSTRACT

Disclosed is an image display system having a plurality of CRT display screens. The system is of the type in which a number of images of specific portions of a patient having a specific ID code are selected from among a multitude of X-ray image taken by a plurality of shooting methods, and when the regions of interest are specified, a plurality of appropriate images are further selected using the previously stored aptitude values for the regions and shooting methods and displayed on said plurality of CRT display screens. In order that the segments to be inspected can be pointed to on the screen on which the image of the patient is displayed, a memory is provided which is adapted to previously store codes corresponding to the specific image of the patient and to specify the respective regions of the image in such a manner that they correspond to the pixel positions of the image.

5 Claims, 8 Drawing Sheets

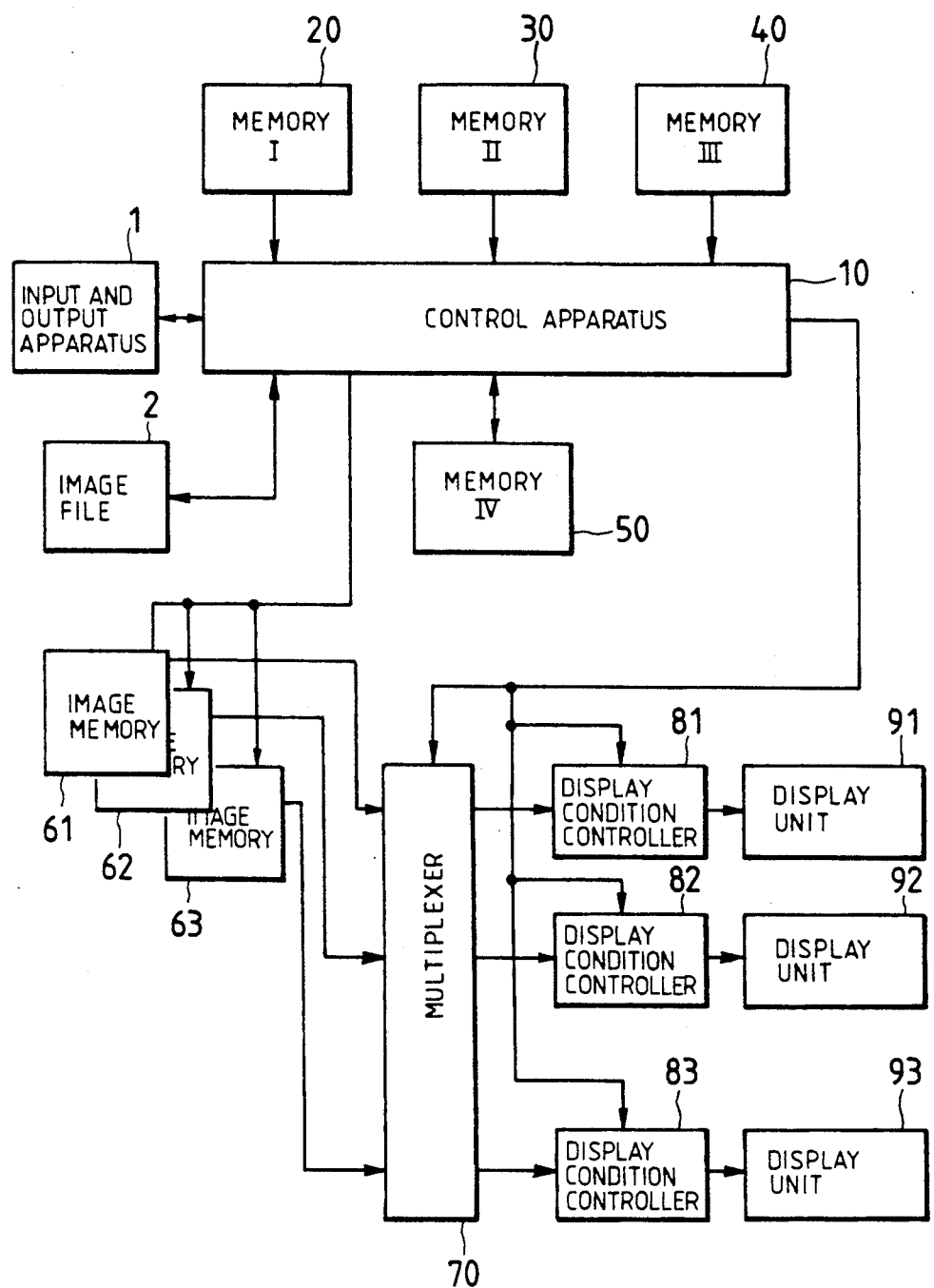

| ORDER OF APTITUDE | CODE OF SHOOTING METHOD | ADDRESS IN IMAGE MEMORY | ASSIGNMENT OF DISPLAY UNITE | DISPLAY CONDION |
|---|---|---|---|---|
| 1 | f | #i | #3 | |
| 2 | a | ∅ | — | |
| 3 | c | #(i+2) | #1 | |
| 4 | e | #(i+4) | #2 | |
| 5 | d | #(i+6) | . | |
| 6 | b | #(i+1) | . | |
| 7 | g | #(i+9) | #n | |
| ⋮ | ⋮ | ⋮ | ⋮ | |

|   |   |   |   |   |   |   |   |   |   |
|---|---|---|---|---|---|---|---|---|---|
| 0 | 0 | 0 | 0 | 0 | 0 | 0 | 0 | 0 | 0 |
| 0 | 0 | 0 | 1 | 1 | 0 | 0 | 0 | 0 | 0 |
| 0 | 0 | 2 | 2 | 2 | 0 | 0 | 0 | 0 | 0 |
| 0 | 0 | 3 | 3 | 3 | 0 | 0 | 0 | 0 | 0 |
| 0 | 0 | 3 | 3 | 3 | 0 | 0 | 0 | 0 | 0 |
| 0 | 3 | 3 | 3 | 3 | 0 | 0 | 0 | 0 | 0 |
| 0 | 4 | 4 | 4 | 4 | 0 | 0 | 0 | 0 | 0 |
| 0 | 4 | 4 | 4 | 4 | 0 | 0 | 0 | 0 | 0 |
| 0 | 4 | 4 | 4 | 4 | 0 | 0 | 0 | 0 | 0 |
| 0 | 4 | 0 | 0 | 0 | 0 | 0 | 0 | 0 | 0 |

FIG. 7B

| CODE | NAME OF REGION |
|------|----------------|
| 0 | (BACK GROUND) |
| 1 | APEX OF LUNG |
| 2 | UPPER REGION OF LUNG |
| 3 | MIDDLE REGION OF LUNG |
| 4 | LOWER REGION OF LUNG |

IMAGE DISPLAY SYSTEM AND DATA INPUT APPARATUS USED THEREIN

BACKGROUND OF THE INVENTION

The present invention relates to an image display system for X-ray images, etc., and more particularly, relates to a display control method making it possible to display images of a combination suited for interpretation when the region of interest is specified, with the most appropriate arrangement and the best image quality.

Images utilized for medical purposes include X-ray images, CT (computerized tomography) images, ultrasonic images, etc., all of these images being utilized by physicians for the purpose of conducting diagnosis of diseases. Various systems have been devised in which these images are generally prepared on an on-line basis. In such systems, images are reproduced, for example, on a CRT display apparatus, diagnosis being enabled by observation of these images. With regard to X-ray images, for example, the dynamic range and resolution of the display images on a CRT display apparatus is not satisfactory, as compared with images developed on X-ray films. Consequently, it is necessary to set the display condition, such as gray level transformation and spatial frequency enhancement, to the most appropriate conditions, in accordance with the region of interest and the diagnosis purposes.

Japanese Patent Laid-Open No. 28144/1984 discloses an apparatus in which an X-ray image of a patient recorded on a recording medium such as storage phosphor is displayed as a visible image on another recording medium (e.g., photographic film) or on a display apparatus such as a CRT, automatically selecting the best suited display conditions (e.g., gray level and spatial frequency enhancement) by inputting data such as the portion and the shooting method.

The above prior art system is attended with the following problems:

(1) Diagnosis is performed using a plurality of images. Images taken by different shooting methods and in different directions of vision are observed and compared with each other. Or, after observing some portion (e.g., a front view of the entire chest), a region where there is some abnormality (e.g., the apex of a lung) is observed. Accordingly, a single diagnosis requires a number of input operations, selecting each time the regions of interest and the shooting methods.

(2) The above input operation is conducted by manipulating the keyboard or pointing to the positions concerned on the displayed icon. In any case, the operator has to turn his gaze from the image of the patient he is obserbing so as to be able to manipulate the keyboard or perform the operation of pointing to the region of interest and the shooting method, and watching the above icon, which reduces the efficiency of the diagnosis.

SUMMARY OF THE INVENTION

It is an object of this invention to provide an image display system relieving the bother for the operator, thereby enabling efficient diagnosis.

Another object of this invention is to provide an image display system in which a plurality of images suited for the diagnosis of the portion or region of interest are automatically selected by a single pointing operation of the portion or region of interest.

Still another object of this invention is to provide an input means making it possible to point to a region to be minutely observed and input it to the system without taking one's eyes from the image that is being observed.

A system featuring this invention comprises an original image file storing a multitude of images, a first memory adapted to store the relation between the shooting methods for the portion of a subject and the names of the describable region, a second memory adapted to store the anatomical positional relationship between images obtained by the different shooting methods, a third memory adapted to store the display conditions suited to interpretation of the region of interest in the image, a fourth memory adapted to store for each patient the data on the images to be interpreted such as the shooting method, a multiplexer adapted to allot the images to said plurality of displays, and an display condition controller adapted to convert X-ray images into display images, wherein the image for interpretation of the region of interest is selected by the name of the region of interest and said first and fourth memories, the positional relationship in display and the display conditions for the image thus selected are selected from said second and third memories, and the image suited for interpretation of the region of interest is output to a plurality of displays situated at positions suited for diagnosis.

In accordance with another feature of this invention, an apparatus is used as an input means for inputting said region of interest to the system, which apparatus comprises a position pointing means for indicating positions concerned on the display, a memory adapted to store mapping information in which a region code is previously alloted to each segment of the original image to be displayed, a read-out controller adapted to access said memory in accordance with the pointing signal of said position indicating signal so as to read out the segment name and input it to said system.

BRIEF DESCRIPTION OF THE DRAWINGS

FIG. 1 is a block diagram showing an embodiment of the image display system of this invention;

FIGS. 7A to 7C are charts illustrating the preparation of the mapping information of FIG. 6.

DETAILED DESCRIPTION OF THE PREFERRED EMBODIMENTS

Figures 2A, 2B:
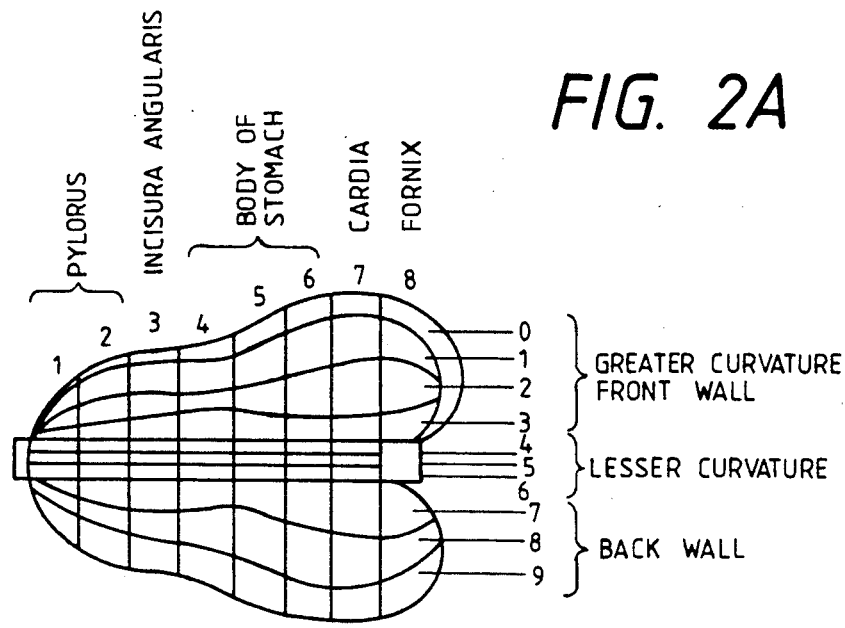
FIGS. 2A and 2B are charts showing the stomach region division and the relation between the regions and the shooting methods, respectively.

FIG. 1 is a block diagram of the display control system which is an embodiment of the present invention. As shown in FIG. 1, this system comprises a control apparatus 10 adapted to control the entire system, an input and output apparatus 1 adapted to input information to the control apparatus 10 and to output the processing result, an image file 2 adapted to store the (original) images of various portions of a number of subjects taken by various shooting methods, said images being thus stored at respective addresses, a first memory 20 adapted to store the relation between the shooting methods and the names of the describable regions, a second memory 30 adapted to store the anatomical positional relationship between images taken by different shooting methods, a third memory 40 adapted to store the display conditions suited to interpretation of the regions of interest of each image, a fourth memory 50 adapted to store attributes such as the shooting method used for the images of regions of interest, image memories 61 to 63 adapted to receive the data on the images to be displayed, a multiplexer 70 adapted to distribute the display information to a plurality of display devices, display condition controllers 81 to 83 adapted to store the display conditions such as the gray level processing and the frequency enhancement for each section and to convert the image quality into that for the display device, and a plurality of display units 91 to 93.

The first memory 20 will now be described with reference to FIGS. 2A and 2B.

The human stomach may be divided into 77 segments, as described, for example, in "The Stomach and the Intestines 14 (10)" of "Screening in Cancer" by Heizaburo Ichikawa, 1979. As shown in FIG. 2A, the stomach can, when developed in a plane, be divided laterally into pylorus 1 and 2, incisura angularis 3, bodies of stomach 4, 5 and 6, cardia 7, and fornix 8, and longitudinally into greater curvature 0, front walls 1, 2 and 3, lesser curvatures 4, 5 and 6, and back walls 7, 8 and 9. Of the 8 (lateral) × 10 longitudinal) = 80 segments, the lesser curvatures 4, 5 and 6 cannot be divided with respect to the fornix 8, so that the number of segments amounts to 77 in all.

As for the stomach shooting methods, they are, roughly speaking, of three types: mucosal relief method, full stomach method and double contrast method They can be subdivided in terms of the poses of body and the directions of X-rays, so that the number of methods amounts to 24 in all. As for the postures, they can be classified into the upright, the prone and the supine positions. Since there are front and oblique positions for each of the above three postures, the number of postures amounts to 24 in all.

The relation between these segments and shooting methods may, for example, be expressed in a matrix form shown in FIG. 2B. The value P showing the degree of aptitude of each shooting method for interpretation or observation of each segment (hereinafter referred to as the aptitude value) can be expressed in a numerical value ranging from 0 to 1. This value P is 1 for the best suited method and 0 for an irrelevant one (uninterpretable). Naturally, various values exist between 0 and 1, viz., 0.6, 0.7, 0.8, 0.9 for relatively suited ones and 0.1, 0.2, 0.3, 0.4 for rather irrelevant ones. The value is 0.5 when it is not to be seen whether it is relevant or not.

While the above description has been made with respect to the stomach, such aptitude values can be previously determined for other internal organs, in terms of the regions and the shooting methods thereof. In the first memory 20 shown in FIG. 1, the codes of the different regions and those of the various shooting methods are stored in a matrix-like form along with the respective aptitude values.

With reference to FIG. 2A, the front walls are described as $m_{4-6}^{1-3}$. This manner of expression is adopted for describing the regions that can be interpreted by the shooting methods. Such data are stored in the second memory 30 as anatomical information.

In this display control system, the display conditions for each shooting method and for each region such as the gray level processing and the frequency enhancement are expressed in the matrix form as in FIG. 2B, each factor being stored in the third memory 40 in the form of a conversion table or a conversion formula.

As to the portion of body and the shooting methods, they are input to the system as the image data along with the patient ID (identification number) by means of menu selection, etc. and stored in the fourth memory. Naturally, it is also possible to automatically extract the names of said portion of body, the shooting methods, the names of the regions pointed to by the interpreter, etc., by an image recognizing apparatus.

Figure 3:
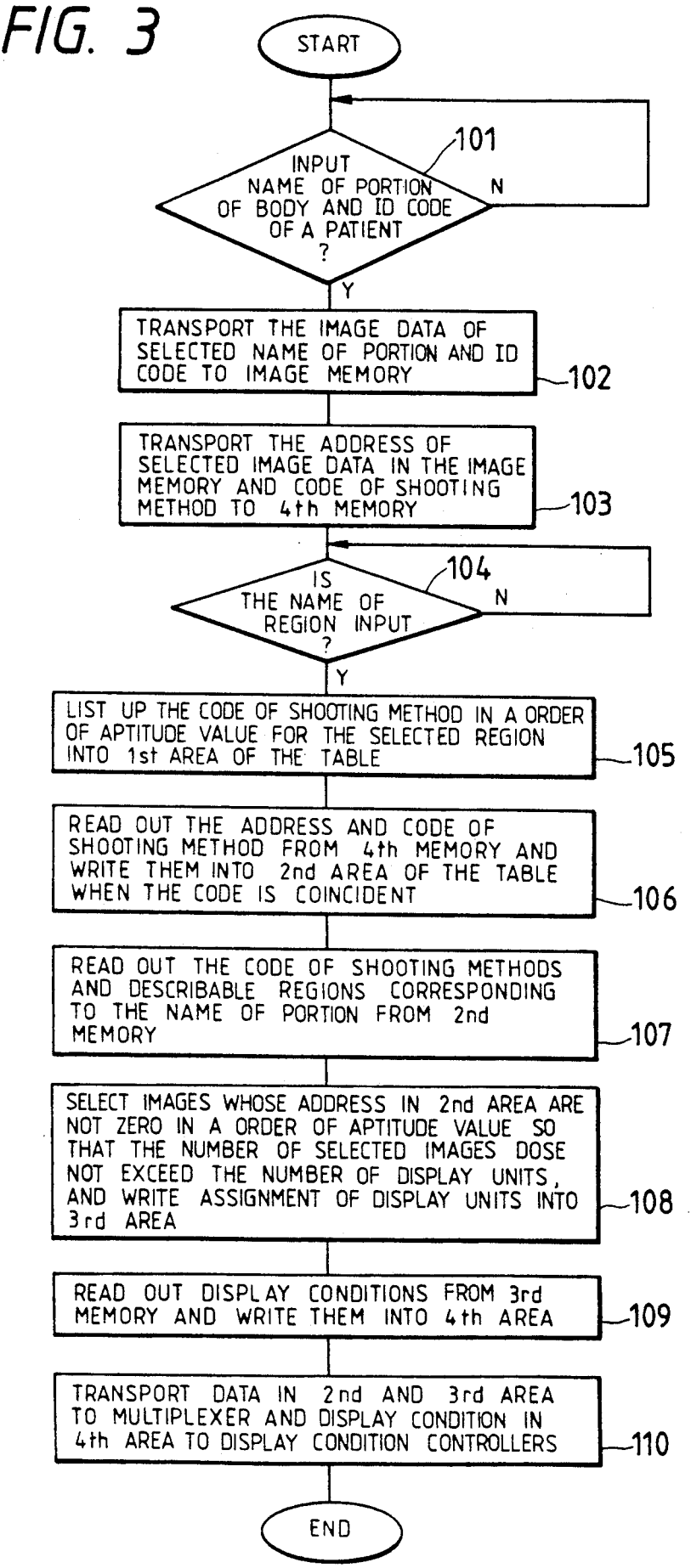
FIG. 3 is an operational flowchart of the control apparatus shown in FIG. 1.

The procedure of processing in the control apparatus 10 of this display control system will now be described in detail with reference to FIGS. 3 and 4.

First, the name of the portion of body and the patient ID code are input to the system (Step 101). The control apparatus 10 then transfers the image data on the image corresponding to said name of the portion and the patient ID code to the image memories 61 to 63 from the file 2 (Step 102). Further, the address of the transferred image in the memories 61 to 63 and the code of the shooting method are transferred to the fourth memory 50 (Step 103). The portion may, for example, be the chest, the upper or lower digestive organs, etc. The operation of transferring images to the image memories 61 to 63 and that of transferring data to the fourth memory 50 consist of well-known techniques, so that a detailed description thereof will be omitted.

Next, the name of the region of interest is input through the input and output apparatus 1 (Step 104). The control apparatus 10 then reads out the table of aptitude value (equivalent to the one shown in FIG. 2B) in terms of the shooting method and the region name for the portion designated by the first memory 20 and sorts the shooting methods in descending order for the value of aptitude. Then, as shown in FIG. 4, the table area for storing the order of aptitude, the code of shooting method, the address in image memory, the assignment of display unit and the display conditions is made. After that, the codes of shooting method are listed up in the first area 11 corresponding to the order of aptitude (Step 105). They are, for example, listed up as f, a, c, e, d, b, g, . . . , as shown in FIG. 4.

Subsequently, the control apparatus 10 reads out the code of shooting method relative to the image of the subject as well as the corresponding address in the memories 61 to 63, and when the data read out agrees with the code of the shooting method in said storage area 11, the address in the image memories 61 to 63 is written into the column corresponding to said code of agreement in the second storage area 12 (Step 106). If no image is found among the images of the subject taken by the methods listed up, "0" is written into the corresponding column in the second area 12. In the example shown in FIG. 4, the image taken by the shooting method f ranked in the first order is stored in the address #i of the image memory. Since there is no image taken by the shooting method a ranked in the second order, '0' is stored in the corresponding area. The image taken by the shooting method c ranked in the third order is stored in the address #(i+2), and the image taken by the shooting method e ranked in the fourth order is stored in the address #(i+4).

The control apparatus 10 reads out, based on the region names which have already been input, the table in terms of the shooting methods and the describable regions for the portion, from the second memory 30 (Step 107). Images taken by a shooting method, for which no '0' is stored in the area 12, are selected in the order of aptitude in a number less than the number of the display units. Then, the positional relationship between the images selected is judged based on the table read out from the second memory 30. After that, the numbers of the display units for displaying the selected images are stored in the storage area 13 in the table (Step 108). In the example shown in FIG. 4, there are n display units and it is recorded in the assignment area 13 that the image at the address #i is displayed on the display unit #3, that the image at the address #(i+2) is displayed on the display unit #1, that the image at the address #(i+4) is displayed on the display unit #2, ... and that the image at the address #(i+9) is displayed on the display unit #n.

If in the case of a stomach, for example, a front image of supine double contrast method and a second oblique image of supine double contrast method are included in the selected images, the describable segments of the former may be expressed as the portion surrounded by a part of pylorus, incisura angularis, a part of the bodies of stomach, lesser curvatures and back walls shown in FIG. 2A, i.e. as the part $m_{4\text{-}9}^{2\text{-}5}$, and the describable segments of the latter may be expressed as the part surrounded by part of the bodies of stomach, cardia, lesser curvatures and back walls, i.e. as the part $m_{4\text{-}9}^{6\text{-}7}$. From the comparison of these two expressions with each other, the latter, i.e. the second oblique image of supine double contrast method is placed over the former, i.e. the front image of supine double contrast method.

Subsequently, the control apparatus 10 reads out, based on the name of the portion which has already been input, the display condition table in terms of the shooting methods and the regions for the portion, from the third memory 40. The display conditions for the images taken by the shooting methods selected in the above processing are obtained, based on the region names which have already been input, said display conditions being stored in the storage area 14 of the table shown in FIG. 4 (Step 109).

FIG. 5 illustrates an example of the display condition table prepared in terms of the shooting methods and the region names stored in the third memory 40.

Figure 5A:
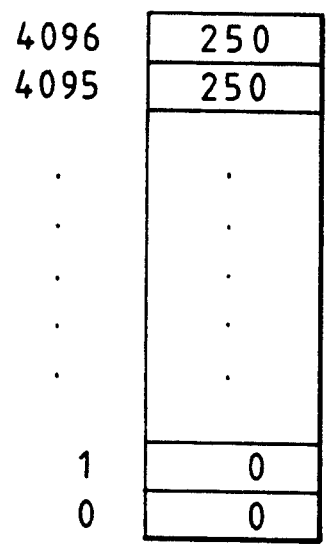
FIGS. 5A and 5B are diagrams showing an example of the display condition table used in the image quality converter of FIG. 1.
Figure 5B:
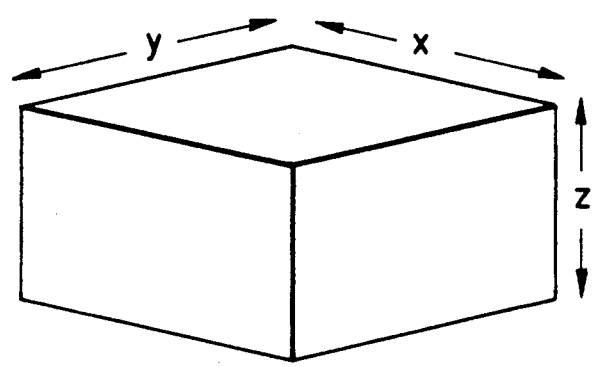

As shown in FIG. 5B, an image may be represented with the plane in the X-Y directions and the information depth in the Z-direction, i.e. the image density.

An X-ray image has gray levels 0 to 4,096. However, CRT or liquid crystal displays can only express gray levels 0 to 256, so that prior to the image transfer to the display units 91 to 93, the display condition controllers 81 to 83 prepare conversion tables in which the image levels 0 to 4,096 correspond to the display levels 0 to 256. As shown in FIG. 5A, for example, the image levels 0-3 correspond to the display level 0, the image levels 4,093-4,096 correspond to the display level 256, and the intermediate levels correspond to the respective display levels in the same way. Further, in the image plane, the bone regions are white and the stomach itself is black. Since other regions than these do not require observation, the display becomes more effective if they are eliminated. For this purpose, the regions to be eliminated are to be designated beforehand.

Subsequently, the control apparatus 10 transports the contents of the storage areas 12 and 13 of the table prepared in the procedure shown in FIG. 4 to the multiplexer 70, and, based on the contents of the storage area 13, transports the display conditions of the storage area 14 to the display condition controllers 81 to 83 so as to control the quality of the images to be displayed on the display units 91 to 93 (Step 110).

Since well-known devices are employed for the multiplexer 70, the image quality converters 81 to 83 and the display units 91 to 93, a detailed description thereof is omitted here.

Thus, in accordance with this embodiment of the present invention, it suffices to input and store, on a plurality of subjects the relation between the shooting methods and the interpretable regions, the anotomical positional relationship between the shooting methods, the display conditions suited for interpretation of the region concerned, and the image data on the portion and the shooting methods for the image taken, to enable a completely automatic sorting out and control of the image taken by the best suited shooting method and the best suited display unit on which the image is to be displayed. Furthermore, an efficient and accurate interpretation can be conducted even with a display device composed of a limited number (e.g., 6 to 8) of CRT displays, which are not always suited for displaying X-ray images.

While in this embodiment has been described as applied to X-ray images taken by various shooting methods, it is naturally to be understood that for other modalities, for example, in the case of tomograms by an X-ray CT, MRI (magnetic resonant imaging), etc., the image in the vicinity of the region of interest can be selected from the input information such as the slice surface information, thereby enabling a control similar to the one described above.

In the above described embodiment, it is necessary for the operator to manipulate the keyboard of the input and output apparatus (shown at 1 in FIG. 1) or point positions on an icon which is provided for the purpose, to be able to perform the designation of the region of interest. With such input methods, however, the operator has to turn his eyes from the image on the display every time he manipulates the keyboard or watches the icon, which is undesirable for an efficient diagnosis. A second embodiment overcoming this problem will now be described with reference to FIGS. 6 to 8.

In this second embodiment, one of the plurality of display units 91 to 93 is used as an input apparatus for regions requiring a more minute observation. The block 93' in FIG. 6 is a display unit used as such an input apparatus. The block 110 in FIG. 6 shows an original image selected from the image file 2 in FIG. 1 and transported to one of the image memories 61 to 63. Accordingly, the block 100 in FIG. 6 consists of one of the image memories 61 to 63 in FIG. 1.

As the display apparatus 93', a liquid crystal display may be employed, besides the CRT. A position pointing apparatus 102 is adapted to output addresses corresponding to the positions pointed on the screen of the display 93'. This apparatus 102 may consist of a touch screen or a light pen. Or, it may be a device of the type having a screen cursor movable by means of a mouse, a tracking ball, etc.

A memory 103 consists of a memory for an ordinary computer, storing mapping information 130 accurately corresponding to the images which is being obserbed.

A read-out controller 104 is adapted to refer to the mapping information 130, based on the information from the position pointing apparatus 102, and output names or attributes to an output line 105. This read-out controller 104 may be realized with the hardware and software of a general purpose computer.

Names or attributes from the read-out controller 104 are utilized in the control apparatus 10 in FIG. 1. They are utilized in the control apparatus 10, for example, in the following manner:

(a) When the name of a region is output from the read-out controller 104, another image of the same region of the patient concerned is accessed using the name thus output and displayed.

(b) When an image display parameter (such as contrast) is output from the read-out controller 104 as a kind of attribute on a region, the display is adjusted, using this parameter, such as to be the best suited for observing that region.

The mapping information used in this embodiment will now be described in detail.

Figure 7C:
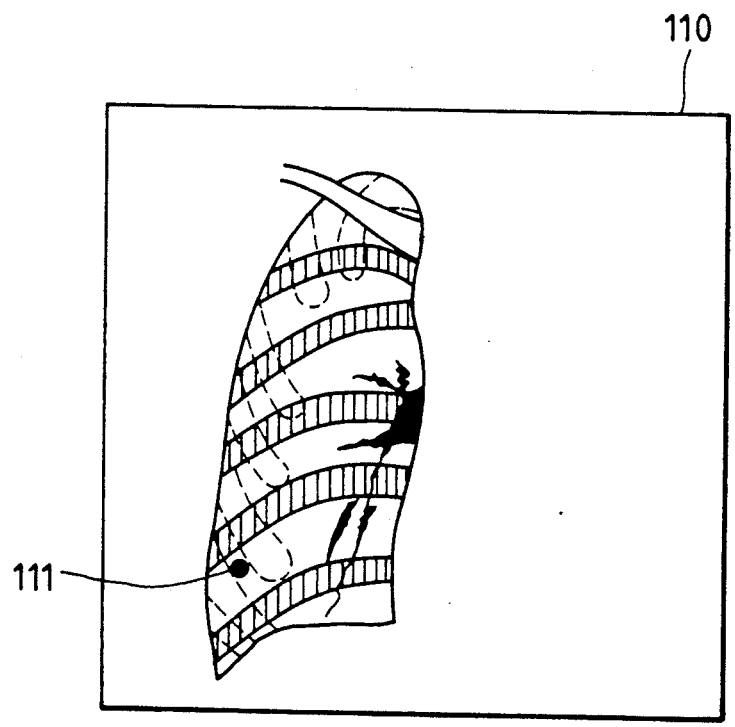

FIGS. 7A, 7B and 7C are, respectively, a code storage chart of the mapping information used in this invention, a correspondence chart of codes and region names, a diagram showing an example of region to be designated by a pointing device.

Prior to the input operation, mapping information as shown in FIG. 7A is prepared for each image to be observed. The mapping information indicate names of portions in the image corresponding to the pixels of the image observed. These names are codified and stored in a two-dimensional memory, in areas corresponding to the pixels of the image.

In this example, mapping information indicating with codes of the regions in the corresponding positions with respect to an image 110 of a single lung as shown in FIG. 7C, is stored in the memory 103 in such a manner as shown in FIG. 7A. As shown in FIG. 7B, code 0 corresponds to the background, code 1 the apex of lung, code 2 the upper region of lung code 3 the middle region of lung, and code 4 the lower region of lung. Although in FIG. 7A the number of codes is shown as 10×10 for the sake of convenience, the same number of codes as that of the pixels of the image to be observed is stored actually.

Since in this embodiment the pixels of the image to be observed and the codes show one-to-one correspondence, codes can be easily obtained from the mapping information. In other words, when a certain pixel 111 of the image observed is pointed by a position pointing apparatus, the code stored in the corresponding area can be read out and output from the mapping information 130 of FIG. 7A. Here, the code 131 (lower lung 4) at the position shown by the crosshatching in FIG. 7A is output.

While FIG. 7A shows an example of mapping information 130, other mapping information 130 may, for example, be divided and stored in a plurality of storage areas for each name of region.

The method of preparing this mapping information 130 will now be described in detail.

The mapping information 130 is prepared from the image 110 to be observed. The preparation is enabled, for example, through application of the technique for automatically recognizing an X-ray image. As an example of such an automatic recognition technique, a method of automatically discriminating tissues (specifically, heart, ribs, etc.) intended for chest X-ray images is proposed by Toriwaki et al. in "Medical Image Processing", Asakura Shoten, 1982, pp. 115-121.

According to this method, mapping information is prepared by the following procedure:

(a) First, by examining the variation in the average density with respect to the vertical and horizontal directions, a rectangle circumscribing the lung area is determined. In other words, an oblong rectangle is moved downwards from above with respect to the image 110 to be observed, successively deciding whether each position it passes is part of the lung or not, from the density thereof. By this operation, the upper and lower ends of the lung are detected. Subsequently, a longwise rectangle is moved from the left to the right in the same way as the above operation, thereby detecting the left and right ends of the lung. By this procedure, an external rectangle surrounding and in contact with the lung is obtained.

(b) Subsequently, the contour of the lung is determined by the edge extraction method. In other words, an accurate contour in accordance with the pixel density is formed along the external rectangle obtained in the above (a). When, for example, the background density is 10 and the lung density is 100, the points corresponding to the density difference of 10:100 are successively linked with one another, thereby forming the contour of the lung.

(c) Several characteristic points are extracted by template matching. In other words, a predetermined model (template) is set up as the standard which is applied along the contour. In the case of a lung, for example, the left and right ends are important as the characteristic points, i.e., after locating the left and right ends as well as the lower end of the lung, the upper end thereof is located, thus determining a distinctive form of the lung.

(d) Based on the characteristic points obtained in the above (c), the contours of the clavicle and ribs are determined by the edge extraction method. For example, the clavicle is situated above the lung and a plurality of ribs are surrounding the lung. The contours of these bones are prepared by linking the points corresponding to the density difference.

(e) Based on the contours obtained in the above (c) and (d), the segment names corresponding to the points on the images are determined. For example, the apex of the lung is a part of the lung situated above the clavicle, so that to the portion surrounded by the lung contour obtained in (c) and the clavicle contour obtained in (d) is alloted code 1 representative of the apex of the lung. The other parts are also furnished with the respective codes in a similar manner.

By the above procedure, the mapping information in which, as shown in FIG. 7A, all the parts of the lung, from the apex to the lower region of lung, are represented with codes is prepared. Specifically, the prepared area codes 1 to 4 are registered in the memory 103 and utilized as the mapping information 130.

The above-described method enables an automatic preparation of the mapping information 130 by means of a computer. Naturally, it is also possible to manually prepare the mapping information 130.

The method in accordance with this invention of inputting the segment names using the mapping information 130 will now be described.

Figures 4, 6:
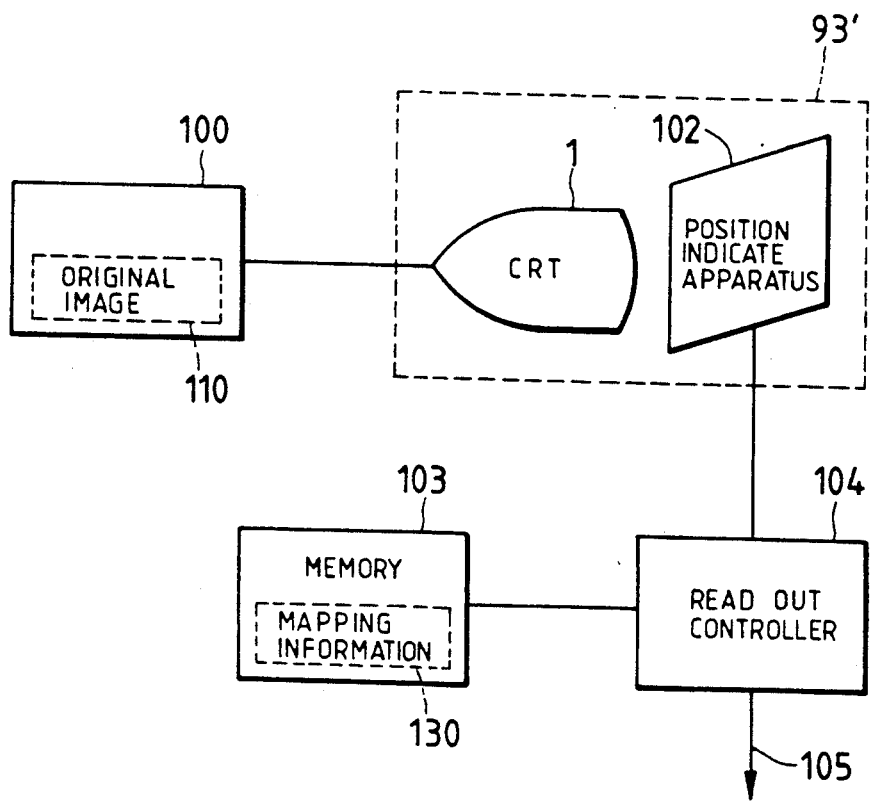
FIG. 4 is a chart illustrating the assignment of the storage areas prepared by the control apparatus shown in Fig. 1.
FIG. 6 is a diagram showing another example of the input apparatus of FIG. 1.

First, with reference to FIG. 6 showing the input apparatus, the operator points positions on the original image by means of the position pointing apparatus 102. This causes the positional information to be transmitted from the position pointing apparatus 102 to the read-out controller 104, which calculates, based upon the positional information transmitted, the corresponding address of the memory 103. Next, based on the calculated address, the mapping information in the memory 103 is accessed. Subsequently, the code obtained from the mapping information 130 is transmitted to the output line 105 and input to the control apparatus 10 shown in FIG. 1.

When the region of interest is designated by the operator by the above procedure, the read-out controller 104 reads out the code of the corresponding regions from the mapping information 104. The code thus read out is input to the control apparatus 10.

Figure 8A:
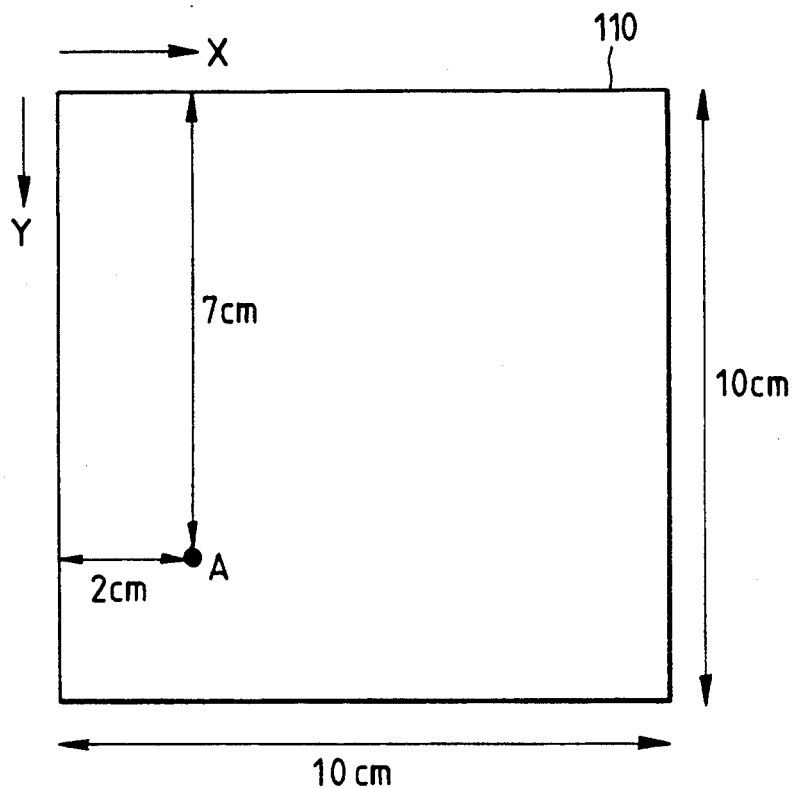
FIGS. 8A and 8B are charts illustrating the method of transforming positional information into addresses of the mapping information.
Figure 8B:
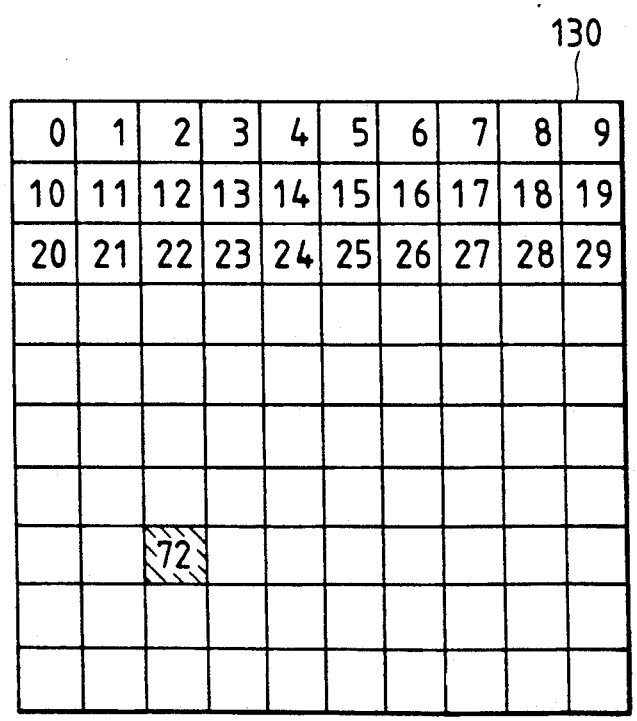

FIGS. 8A and 8B illustrate the method of calculating addresses from positional information. Of these figures, FIG. 8A shows the positional information from the pointing apparatus 102, i.e. the position of the original image 110 on the CRT display and FIG. 8B shows the address assignment condition of the mapping information 130 stored in the memory 103.

As shown in FIG. 8A, for example, the original image 110 is assumed to have a size of 10 cm × 10 cm, and the position A in the image thereof is pointed at the position situated 2 cm from the left and in the X-direction and 7 cm from the upper end in the Y-direction. The position pointing apparatus 102 transmits the designated position, as described above, as information in terms of the distances in the X- and Y-directions to the read-out controller 104.

The memory 103 in which the mapping information 130 is stored is set as a memory having 10 × 10 addresses so that the address of a position corresponding to the positional information from the position pointing apparatus 102 can be calculated with ease. In other words, the addresses are successively allocated in the X-direction from the left upper end of the memory, as address 0, address 1, address 2, . . . , address 9. Then, from the left end one step lower in the Y-direction, as address 10, address 11, address 12, . . . , address 19. Then, another step lower in the Y-direction, as address 20, address 21, . . . , address 29. In this way, addresses 0 to 99 are allocated in the memory.

When the position of point A is transmitted from the position pointing apparatus 102 to the read-out controller 104 as "X2 cm, Y7 cm", the address is obtained by multiplying the number in the Y-direction by 10 and adding the number in the X-direction to the product. In other words, the corresponding code can be read out by accessing address 72 (=7×10+2). By thus establishing a simple positional correspondence between the original image and the mapping information, any region pointed can be immediately converted into a memory address of the mapping information, the corresponding code is read out and the code representative of the pointed region is input to the system.

What is claimed is:

1. An image display system adapted to display X-ray images of the portions of a subject on a plurality of display screens, comprising a first memory adapted to store the relation between the shooting methods for the portion and the ames of the describable regions, a second memory adapted to store the anotomical positional relationship between images obtained by the different shooting methods, a third memory adapted to store the display conditions suited to interpretation of the regions to be inspected, a fourth memory adapted to store for each patient the data on the images to be interpreted such as the shooting method, a multiplexer adapted to assign the images to said plurality of displays screens, and an display condition controller adapted to convert X-ray images into display images, wherein the image for interpretation of the region of interest is selected by the name of the region of interest and said first and fourth memories, the positional relationship for display and the display conditions for the image thus selected are selected from said second and third memories, and the image suited for interpretation of the region of interest is output through said multiplexer and said display condition controller to a plurality of display screens situated at positions suited for diagnosis.

2. An image display system as claimed in claim 1, further comprising, as an input means for said region of interest, a display apparatus adapted to display the original image of said patient and having a position pointing means for pointing to positions on the display screen of said image, a fifth memory adapted to store in advance map information consisting of the respective codes for specifying a plurality of segments obtained by dividing said original image, and a read-out control means adapted to read out the codes for specifying segments from said fifth memory.

3. An image display system adapted to display a plurality of images on a plurality of display screens comprising:
a plurality of display devices each having a display screen;
an image file which stores image data of original images of various portions of a body, taken by a plurality of shooting methods;
a plurality of image memories each for receiving and storing image data of each of a plurality of selected original images;
a multiplexer which distributes selected image data in said image memories respectively to said display devices;
a first control data memory storing tables for respective portions of a body, each table containing a matrix indicating relations between a plurality of shooting methods for taking images of a corresponding portion of a body and a plurality of regions in corresponding portions of a body, each term of said matrix is a value of aptitude of a corresponding shooting method for interpretation or observation of a corresponding region;
a second control data memory storing at lest first and second codes for each of said original images stored in said image file, said first code identifying a name of a portion of a body depicted in the corresponding original image, said second code identifying a shooting method adopted for taking the corresponding original image;
input means for inputting a specified first code to specify a portion of a body and for inputting a specified region of interest;

a control apparatus connected to said image file, said image memories, said multiplexer, said first and second control data memories and said input means, which control apparatus operates to select original images that have a first code coincident with said specified first code input by said input means by searching said second control data memory and to transfer image data of selected original images from said image file to said image memories when said specified first code is input, and which looks-up a corresponding table in said first memory using said specified region of interest as a key and sorts a plurality of shooting methods in said corresponding table in decreasing order of the value of said aptitude when said region of interest is input, and also which further selects original images of a number not exceeding the number of said display devices among the images transferred to said image memories by referring to sorted shooting methods and controls data distribution of said multiplexer according to the further selection.

4. An image display system as claimed in claim 3, further comprising a display apparatus adapted to display the original image of said patient and having a position pointing means for pointing to positions on the display screen of said image, a third control data memory adapted to store in advance map information consisting of the respective codes for specifying a plurality of segments obtained by dividing said original image, and a read-out control means adapted to read out the codes for specifying segments from said third control data memory.

5. An image display system according to claim 3, wherein said second control data memory stores a third code identifying a name of a patient depicted in the corresponding original image, and said control apparatus operates in response to inputting of said first code and said third code to transfer selected image data from said image file to said image memories.

* * * * *